United States Patent
Park

(10) Patent No.: US 6,203,844 B1
(45) Date of Patent: Mar. 20, 2001

(54) PRECOATED POLYMERIC PROSTHESIS AND PROCESS FOR MAKING SAME

(76) Inventor: Joon B. Park, 1810 Country Club Dr., Coralville, IA (US) 52241

( * ) Notice: Subject to any disclaimer, the term of this patent is extended or adjusted under 35 U.S.C. 154(b) by 0 days.

(21) Appl. No.: 09/283,651

(22) Filed: Apr. 1, 1999

(51) Int. Cl.[7] ............................... A61L 27/00; A61F 2/30
(52) U.S. Cl. ..................... 427/2.26; 427/2.24; 427/379; 427/393.5; 427/195; 623/16
(58) Field of Search ................ 623/17.11; 427/2.24, 427/2.26, 2.27, 412.3, 375, 379, 393.5, 195

(56) References Cited

U.S. PATENT DOCUMENTS

| | | | |
|---|---|---|---|
| 3,713,860 | 1/1973 | Auskern | 427/2.26 |
| 3,986,212 | * 10/1976 | Sauer | 3/1.91 |
| 4,156,943 | * 6/1979 | Collier | 3/1.9 |
| 4,164,794 | 8/1979 | Spector et al. | 427/195 |
| 4,213,816 | 7/1980 | Morris | 427/2.26 |
| 4,281,420 | 8/1981 | Raab | 427/2.26 |
| 4,351,069 | * 9/1982 | Ballintyn et al. | 3/1.912 |
| 4,454,612 | 6/1984 | McDaniel et al. | 427/2.26 |
| 4,491,987 | 1/1985 | Park | 3/1.91 |
| 4,554,686 | 11/1985 | Baker | 427/2.26 |
| 4,735,625 | 4/1988 | Davidson | 623/16 |
| 4,840,851 | 6/1989 | Gölander | 427/307 |
| 4,888,413 | 12/1989 | Domb | 528/272 |
| 5,035,714 | 7/1991 | Willert et al. | 623/16 |
| 5,061,286 | 10/1991 | Lyle | 623/16 |
| 5,346,495 | 9/1994 | Vargas, III | 606/92 |
| 5,352,732 | * 10/1994 | Howard | 524/789 |
| 5,529,736 | 6/1996 | Shalaby et al. | 264/162 |
| 5,571,202 | * 11/1996 | Mathys et al. | 623/23 |
| 5,593,719 | 1/1997 | Dearnaley et al. | 427/2.26 |
| 5,650,485 | * 7/1997 | Sun et al. | 528/483 |
| 5,874,123 | 2/1999 | Park | |

\* cited by examiner

Primary Examiner—Shrive Beck
Assistant Examiner—Jennifer Kolb
(74) Attorney, Agent, or Firm—Dority & Manning, PA

(57) ABSTRACT

The present invention is directed to a polymeric prosthesis precoated with a bone cement compatible polymer. The bone cement compatible polymer coating, is provided by an activated powder mixture of polymethyl methacrylate and ultra high molecular weight polyethylene which is bonded to the outer surface of the prosthesis by sintering. Once bonded to a polymeric prosthesis in accordance with the present invention, the precoat strengthens the interface between a bone cement and a prosthesis when the prosthesis is later implanted. The inner layer of the prosthesis may be provided of cross-linked UHMWPE powder sintered with virgin UHMWPE powder or fibers to provide a intermediate layer (s) of the coating present on the prosthesis. The precoat also decreases the likelihood that the prosthesis will loosen and break away from the cement over time. The polymeric implant product of the present invention is particularly well suited for use as an acetabular cup or a tibia plateau in replacing hip joints and knee joints respectively.

15 Claims, 4 Drawing Sheets

PRECOATED POLYMERIC PROSTHESIS AND PROCESS FOR MAKING SAME

RELATED APPLICATIONS

This application is related to U.S. patent application to Joon B. Park entitled "Precoated Polymeric Prosthesis and Process for Making Same" filed Jan. 24, 1997, having Ser. No. 08/787,246 now U.S. Pat. No. 5,874,123 and which is incorporated herein by reference.

FIELD OF THE INVENTION

The present invention is generally directed to polymeric implant products. More particularly, the present invention is directed to a polymeric prosthesis for implantation into the body that has been precoated with a bone cement compatible polymer. The bone cement compatible polymer is added to improve the strength of the interface between the prosthesis and a bone cement once the prosthesis is implanted into the body. In general, the present invention is also directed to a process for coating a polymeric prosthesis with a bone cement compatible polymer.

BACKGROUND OF THE INVENTION

Prosthetic devices are artificial devices used to replace or strengthen a particular part of the body. Such devices can be used in humans or animals to repair or replace diseased or damaged bone, allied tissue associated with the bone, and/or joints associated with the bone. Primarily, prosthetic devices are used to correct or prevent skeletal deformities or injuries and to alleviate the pain and discomfort associated with the deformities or injuries.

When implanting a prosthesis, typically a receiving site or cavity is first prepared in an adjoining bone. In particular, the bone can be cut and reamed out in order to accommodate the prosthesis. A bone cement is then mixed and placed in the receiving site or cavity. A prosthesis is positioned in the bone cement, and the bone cement is subsequently cured and hardened affixing the prosthesis to the bone.

In most applications, bone cement is made from an acrylic polymeric material. Typically, the bone cement is comprised of two components: a dry power component and a liquid component, which are subsequently mixed together. The dry component generally includes an acrylic polymer, such as polymethyl methacrylate (PMMA). The dry component can also contain a polymerization initiator such as benzoyl peroxide, which initiates the free-radical polymerization process that occurs when the bone cement is formed.

The liquid component, on the other hand, generally contains a liquid monomer such as methyl methacrylate (MMA). The liquid component can also contain an accelerator such as an amine (e.g., N,N-dimethyl-p-toluidine). A stabilizer, such as hydroquinone, can also be added to the liquid component to prevent premature polymerization of the liquid monomer.

When the liquid component is mixed with the dry component, the dry component begins to dissolve or swell in the liquid monomer. The amine accelerator reacts with the initiator to form free radicals which begin to link monomer units to form polymer chains. In the next two to four minutes, the polymerization process proceeds changing the viscosity of the mixture from a syrup-like consistency (low viscosity) into a dough-like consistency (high viscosity). Ultimately, further polymerization and curing occur, causing the cement to harden and affix a prosthesis to a bone.

Once implanted, a prosthetic device ideally closely assimilates the characteristics of the bone and/or the joint that the device is intended to repair or replace. The implanted prosthetic device should be capable of supporting and withstanding stresses and strains normally imparted to the repaired or replaced bone joints.

The above process for implanting a prosthetic device is generally accepted within the art and has proven to be a successful process for repairing or replacing damaged bones, bone joints and the like. Prosthetic devices, however, can be prone to loosen within the bone cavity over time. In particular, the acrylic bone cement, which is neither as strong nor as viable as bone tissue, has been universally considered the weakest link in the implant design. It has been found that the bone cement can break away from the prosthesis, can break away from the bone, or can develop stress or fatigue cracks when repeatedly exposed to the normal stress and strains supported by the bones.

Due to these problems, attempts have been made to improve the mechanical properties of prosthetic devices and of the cement interface that exists between the device and the bone. For instance, U.S. Pat. No. 4,491,987, which was filed by the current inventor and which is incorporated herein in its entirety by reference, discloses an improved prosthesis and process for orthopedic implantation of the prosthesis. The current inventor's prior patent is generally directed to a prosthesis precoated with a polymeric material that is compatible with bone cement. Once implanted, the precoat provides a stronger interfacial bond between the bone cement and the prosthesis.

The present inventor's prior work provided great advances in the art with respect to the implantation of orthopedic devices, namely orthopedic devices made from metals such as stainless steel, titanium, and cobalt chrome alloys. However, although metallic devices have achieved relatively high degrees of success in repairing joints, these devices are not always well suited for every application. For instance, in some applications, it is preferred to use a more flexible and less rigid material than metal for opposing joint structures. Specifically, polymeric prosthetic devices are particularly well suited for use in replacing the acetabular cup in a hip replacement and replacing the tibia plateau in knee replacements.

Unfortunately, high strength polymeric materials, such as ultra high molecular weight polyethylene (UHMWPE), do not adhere well to conventional bone cement materials. Thus, in order to attach polymeric prosthetic devices to an adjoining bone using bone cement, deep grooves have been formed into the prosthetic devices for forming a mechanical interlock with the bone cement.

Applicant's copending application teaches the use of a pretreatment of the prosthesis with a mixture of a solvent and a monomer, the monomer being the same as the polymer component of the bone cement. A precoat of a bone cement compatible polymer is then applied to the prosthesis. The coating of the bone cement compatible polymer polymerizes with the monomer bonded to the prosthesis and ultimately forms a copolymer between the prosthetic polymer and the precoat polymer.

In other prior art constructions, polymeric prosthetic devices include a metal backing and stem for bonding the devices to a bone using a bone cement. Alternatively, the polymeric devices have been installed into a bone without cement using bone screws. Bony tissue ingrowth has also been proposed in the past as a means for joining a prosthesis to bone.

While the above described methods and constructions for polymeric prosthetic devices have met with varying degrees of success, there remains much room for improvement and variation within the art. Thus, a need exists for a process for implanting a polymeric prosthesis into a prepared area of the body. More particularly, a need exists for a process that strengthens the interface between a bone cement and a polymeric prosthesis for decreasing the likelihood that the prosthesis will loosen and break away from the cement over time. Further, a need also exists for a precoated polymeric prosthesis that will readily adhere to a curing bone cement mixture once implanted into an adjoining bone.

SUMMARY OF THE INVENTION

The present invention provides further improvements in prior art constructions and methods.

Accordingly, it is an object of the present invention to provide a process for precoating a polymeric prosthesis with a bone cement compatible polymer.

It is another object of this invention to provide a precoating process for a polymeric prosthesis which does not require the use of a polymer solvent.

It is another object of the present invention to provide an implant product including a polymeric prosthesis that has been precoated with a bone cement compatible polymer.

Another object of the present invention is to provide a process for bonding a bone cement compatible polymer coating to a polymeric prosthesis.

Still another object of the present invention is to provide an implant product that buffers the stress transfer from a prosthesis to a bone cement and to an adjoining bone by providing a gradual stiffness gradient from the surface of the prosthesis to the bone cement.

Yet another object of the invention present invention is to provide an implant product that minimizes wear of the acetabular cup or tibia plateau surface opposing the femoral head or condylar metal/ceramic prosthesis. Improved wear is provided by a coating which cross-links the UHMWPE powders prior to molding or sintering the coating layer to the surface of the prosthesis.

These and other objects of the present invention are achieved by providing a process for coating a polymeric prosthesis prior to being implanted into the body. The process includes the steps of providing a prosthesis having a shape configured to be implanted into a prepared area of the body. The prosthesis includes a polymeric portion adapted to be attached to an adjoining bone with a bone cement. A coating of a bone cement compatible polymer is sintered to the polymeric portion of the prosthesis. Specifically, the sintered coating of the bone cement compatible polymer provides a stronger adhesion between the bone cement and the prosthesis.

In one embodiment, the polymeric portion of the prosthesis is made from ultrahigh molecular weight polyethylene UHMWPE. Preferably, the bone cement compatible polymer coating applied to the prosthesis is between about 0.1 to about 2 mm thick, has a substantially pore free outer surface, and is made from a sintered blend of an acrylic polymer and UHMWPE. The acrylic polymer, in one embodiment, is polymethyl methacrylate which is mixed with a UHMWPE powder in the presence of a MMA monomer liquid; boiled; and, vacuum dried. Once dried, the UHMWPE, MMA treated powder is again immersed in a MMA/PMMA stock solution having a dibenzoyl peroxide initiator. The resulting mixture is again dried to a powdered end product. The powdered end product is then used to coat a desired area of the prosthesis followed by sintering under a combination of heat and pressure.

The sintered coating has been found to offer an improved surface for binding with conventional bone cements. Further, the coating material lends itself to use in conjunction with useful additives such as reinforcing fibers or separately applied layers of cross-linked UHMWPE powders which impart useful mechanical properties to the installed prosthesis. For example, blended gradients of materials can be formed which offer improved performance and longevity of an installed implant.

These and other objects of the present invention are also achieved by providing an implant product for implantation into the body. The implant product includes an underlying polymeric member having a shape configured to be implanted into a prepared area of the body. The polymeric member defines a surface adapted to be attached to an adjoining bone with a bone cement composition. A coating covers the surface of the polymeric member and is made from a novel activated mixture of UHMWPE and PMMA powders which are sintered with blended powders and result in a molded prosthesis with a bone cement compatible surface layer.

In one embodiment, the polymeric member is polyethylene and the bone cement compatible sintered material comprises a mixture of UHMWPE powder with PMMA powder. As described above, the normally incompatible powders are mixed together with methyl methacrylate in a process which bonds the mixture to a surface of the implant. The sintered mixture layer of UHMWPE with PMMA provides a surface layer having improved properties for bonding with bone cement.

The sintered layer also provides a useful surface which interacts with other materials such as PE fibers or PMMA. Such materials can be added as separate layers or incorporated into compatible mixtures to provide useful gradients of materials, including a cross-linked inner layer of the prosthesis which makes contact with either the femoral head of a hip prosthesis or the condylar portion of a knee prosthesis.

The implant product may be used to replace various bones and bone joints, and is particularly well suited for use as an acetabular cup or a tibia plateau.

Other objects, features and aspects of the present invention are discussed in greater detail below.

BRIEF DESCRIPTION OF THE DRAWINGS

A full and enabling disclosure of the present invention, including the best mode thereof, to one of ordinary skill in the art is set forth more particularly in the remainder of the specification, including reference to the accompanying figures in which.

Figure 1:
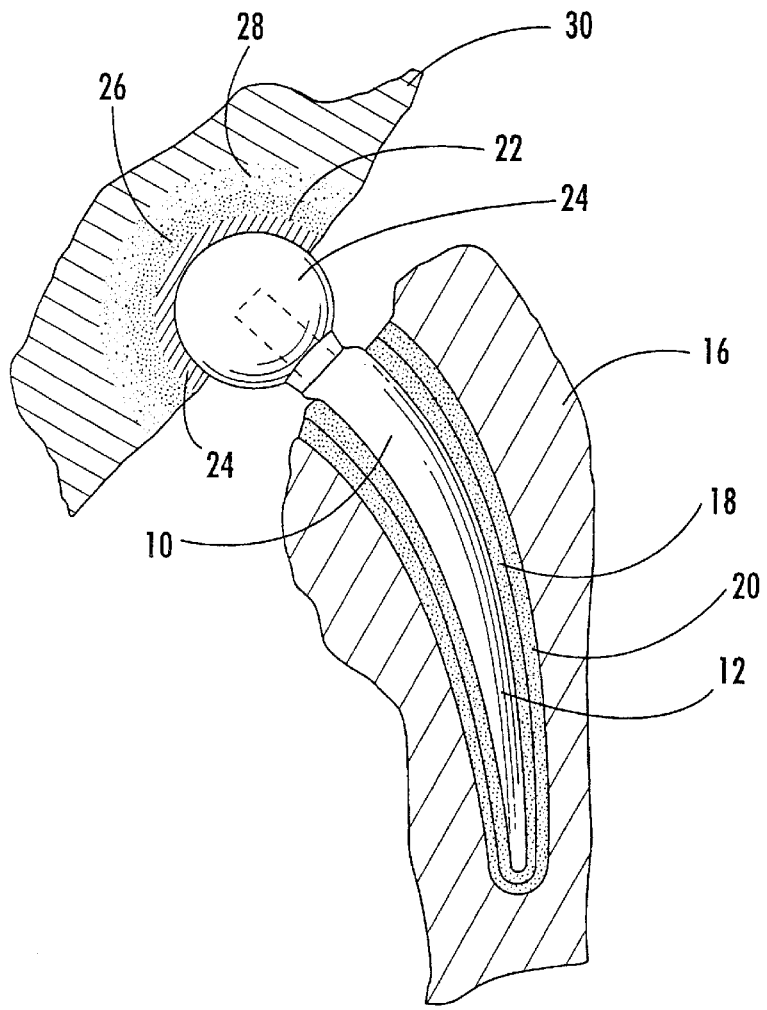
FIG. 1 is a partial cross-sectional view of a total hip implant, illustrating an embodiment of the present invention.

Repeat use of reference characters in the present specification and drawings is intended to represent same or analogous features or elements of the present invention.

DETAILED DESCRIPTION OF PREFERRED EMBODIMENTS

It is to be understood by one of ordinary skill in the art that the present discussion is a description of exemplary embodiments only, and is not intended as limiting the broader aspects of the present invention, which broader aspects are embodied in the exemplary construction.

The present invention generally relates to the orthopedic implantation of polymeric prosthetic devices utilizing a bone cement as a fixative. More particularly, the present invention is directed to a process for precoating a prosthesis with a sintered material having a polymeric component that is compatible with the bone cement used during implantation. The coating provides a strong interfacial bond between the bone cement and the polymeric prosthesis, once the prosthesis is implanted into the body and attached to an adjoining bone.

Besides creating high interfacial strength between the polymeric prosthesis and the bone cement, the precoating improves and facilitates fixation of the implant to an adjoining bone by providing enhanced bonding with the bone cement. The precoating also allows for improved surface coatings which provide for a gradual stress transfer from the surface of the prosthesis to the surface of the adjoining bone due to the gradual change in stiffness from the polymer used to make the prosthesis, to the bone cement, and to the adjoining bone material. Further, by precoating the prosthesis, a lesser amount of bone cement is used during implantation, decreasing the degree of shrinkage the bone cement will undergo when cured and hardened. Ultimately, the precoating improves fixation of the implant and prevents loosening of the implant over time.

The process of the present invention is generally directed to bonding a coating of a bone cement compatible polymer to a polymeric prosthesis. It is believed that, through the process of the present invention, the bone cement compatible polymer coating is sintered to the structural polymer used to make the prosthesis. In one preferred embodiment, the prosthetic precoat is prepared, in part, from the acrylic polymer component of bone cement that is to be used during the operative implantation procedure. For instance, the prosthetic precoat can be made which incorporates polymethyl methacrylate (PMMA).

The prosthesis, on the other hand, can include a polymeric portion or can be entirely made from various polymeric materials. Such materials can include, for instance, polyolefins, such as polyethylene. In one preferred embodiment, the polymeric prosthesis that is bonded to the precoat is made from ultrahigh molecular weight polyethylene (UHMWPE). UHMWPE as defined herein has a molecular weight greater than $2 \times 10^6$ g/mole.

A detailed description of one embodiment of the process of the present invention will now be described. The following process is particularly well suited for precoating a polymeric prosthesis made from polyethylene with a polymethyl methacrylate containing coating. It should be understood, however, that various other polymeric materials can be used to construct the prosthesis and the precoating in accordance with the present invention.

In general, according to the process of the present invention, a polymeric prosthesis, such as made from polyethylene, is contacted with a treated powder mixture. The powder mixture contains an activated mixture of UHMWPE powder with PMMA powder. As used herein, the term "activated" means the powders have been treated so as to provide a compatible mixture in a subsequent sintering process.

A mixture of the activated UHMWPE and PMMA powders is used to coat a surface of the prosthesis. The coating is sintered with heat and pressure to the polymeric prosthesis.

The sintered powder layer precoat should be applied to substantially the entire surface of the prosthesis that is normally designed for immobilized fixation with an adjoining bone. The sintered precoat of the prosthesis may be conducted in any suitable manner that will permit the attainment of a uniform coating over the surface of the prosthetic polymer. Preferably, the coating of the bone cement compatible polymers should be substantially completely polymerized for forming a substantially pore free outer surface. By completely polymerizing the precoat, an improved interfacial bond between the prosthesis and the bone cement is achieved. The sintering temperatures and pressures used promote polymerization of the precoat. Variations of the general protocol may be found in the inventor's published work entitled "*Precoating of Ultrahigh Molecular Weight Polyethylene with Polymethylmethacrylate: Interfacial Strength, Journal of Biomedical Materials Research,* 1998; 43:261–269, incorporated herein by reference, and in a Ph.D. thesis arising out of the inventor's research laboratory by Y. H. Kang, *Pre-coating of Ultrahigh Molecular Weight Polyethylene (UHMWPE) with Polymethylmethacrylate* (PMMA), Ph.D. Thesis, University of Iowa, 1998 also incorporated herein by reference.

The protocol stated above provides an improved bonding surface between the polymeric prosthesis and the bone cement compatible polymer, ensuring that the precoat is firmly attached to the prosthesis. The precoat, comprising a polymer compatible with a polymer component of the bone cement, provides a versatile surface for bonding directly with bone cement or with other useful additives.

The thickness of the bone cement compatible polymer coating will vary depending upon the size of the prosthesis and the particular location where the prosthesis is to be implanted. During implantation, adequate void space should be available between the precoated prosthesis and the bone cavity to enable fresh bone cement to totally surround the prosthesis. In most applications, the coating of the bone cement compatible polymer can be from about 0.1 mm to about 2 mm thick and ordinarily less than 1 mm will prove adequate.

A general protocol useful for this invention is set forth below:

Preparation of Activated UHMWPE/PMMA Powder 50 grams of UHMWPE powder is immersed in an excess of MMA monomer liquid (1000 ml) for 72 hours on a rotary shaker at 25° C. The mixture was followed by boiling for 30 minutes at 100° C. The MAA-treated powder is subsequently air dried in a fume hood for 20 hours followed by vacuum drying for an additional 20 hours.

5 grams of the dried MMA-treated powder is subsequently immersed in 5 mls of a MMA/PMMA stock monomer solution which comprises MMA monomer:PMMA powder at a 9:1 volume to weight ratio, and further containing dibenzoyl peroxide (BPO) initiator at a concentration of 1.5% by weight. The mixture is stirred for 12 hours and the resulting slurry is spread onto a polyethylene plate and vacuum dried at room temperature until the MMA monomer is evaporated. The resulting dried powder is considered "activated" in that the normally incompatible powders of UHMWPE and PMMA are now able to be sintered in combination with additional UHMWPE powders to form a cohesive composition. A mortar and pestle is used to crush the dried powder and sieved to provide a final 90% particle size of 1000 um or smaller.

Sintering is achieved by the application of elevated temperatures and pressure using conventional methods. One useful combination of temperatures and pressure include the use of a temperature range of between 134° to 182° C. and at a pressure of about 19 to 77 MPa. One commercially available polymethyl methacrylate polymer well suited for use in the present invention is DUZ ALL marketed by Coralite Dental Products which includes a polymethyl methacrylate powder that self-cures when mixed with a methyl methacrylate monomer liquid. When mixed and used in the process of the present invention in forming the treated powder pre-coat, the polymer powder and an excess of liquid monomer can be combined in a ratio (weight of polymer powder (g): volume of liquid monomer(ml)) of from about 1:2 to about 1:4. A polymerization initiator, such as benzoyl peroxide, can be present at 1.5% by weight in the polymethyl methacrylate powder. An accelerator, such as N,N-dimethyl-p-toluidine can be present in the liquid monomer for facilitating polymerization of the polymethyl methacrylate polymer.

According to the present invention, once a first precoating of the activated powder is placed and sintered on the prosthesis, further polymeric coatings may be subsequently applied if desired. For instance, further layers of the activated powder having the bone cement compatible polymer can be applied to the prosthesis in order to increase the overall thickness of the precoat. Also, various layers of different polymeric materials can be applied to the surface of the prosthesis in order to facilitate later bonding with a bone cement or to provide the precoated implant product with desired mechanical properties such as wear.

Prosthesis units which have been precoated according to the process of the present invention provide an improved implant product which can be implanted into the body as desired. When the implant product is implanted, first, a receiving site is prepared in an adjoining bone. The two components of the bone cement are then mixed and kneaded until a doughy consistency is obtained. A mixing-kneading time of about four minutes is recommended. The doughy cement is forced into the bone cavity with enough force and pressure to place the cement in the prepared bone bed. Once the precoated prosthesis is placed in the receiving site, the bone cement is cured and hardened.

Once the implant product of the present invention is implanted into the body, the bone cement compatible sintered polymer coating provides a stress/strain gradient that assists in distributing the loads placed on the implanted bone. More particularly, the sintered coating buffers the stress transfer from the prosthesis to the bone cement and ultimately from the bone cement to the bone by providing a gradient of stiffness from the surface of the prosthesis to the bone cement. Further, the precoat forms an improved bond between the bone cement and the prosthesis. According to the present invention, it is believed that a gradient of polymeric layers is established between the polymeric prosthesis and the bone cement compatible sintered polymer layer(s). The established gradient is believed to transfer load from the prosthetic surface to the bone cement more gradually.

Useful properties were observed by sintering the multi-layered structure together at a high temperature and pressure. However, it is thought that even greater improvements in the useful properties may be achieved by applying layers of materials in separate application and sintering steps, and thereby achieve a more uniform product.

By carefully controlling the conditions at which bonding occurs between the polymeric prosthesis and the bone cement compatible polymer, the stiffness gradient occurring in the outer layer of the prosthesis can be carefully controlled as desired. Specifically, implant products with different stiffness gradients may be preferred depending upon the placement of the prosthesis and various other factors. The stiffness gradient can be altered and modified by blending different polymeric materials together in forming the precoat of the present invention and in varying the thickness of those layers. The precoat comprises at least one sintered layer on the prosthetic surface. In one embodiment, the entire polymeric prosthesis itself can be made having a sintered precoat comprising one or more bone cement compatible layers.

By providing a stiffness gradient between the prosthesis and the bone cement, the precoat of the present invention not only strengthens the bond between the prosthesis and the bone cement but also serves to prevent loosening of the implant over time.

Although capable of being used in any suitable application, the polymeric implant product of the present invention is particularly well suited for load bearing joint implants, such as the acetabular cup of a total hip implant, a tibia plateau of a knee joint or the cup in a shoulder replacement. Referring to FIG. 1, a total hip implant is illustrated. The hip implant includes a hip prosthesis 10 having a stem 12 and a head 14. Hip prosthesis 10 is made from a polymeric material having a precoat according to the present invention. As shown, hip prosthesis 10 has been inserted into a cavity defined by a bone 16, such as a femur.

The hip implant illustrated in FIG. 1 further includes a precoated polymeric acetabular cup 22 made in accordance with the present invention. Acetabular cup 22 is more particularly illustrated in FIGS. 2 and 3. As shown in FIG. 1, acetabular cup 22 is adapted to receive head 14 of hip prosthesis 10.

Figure 2:
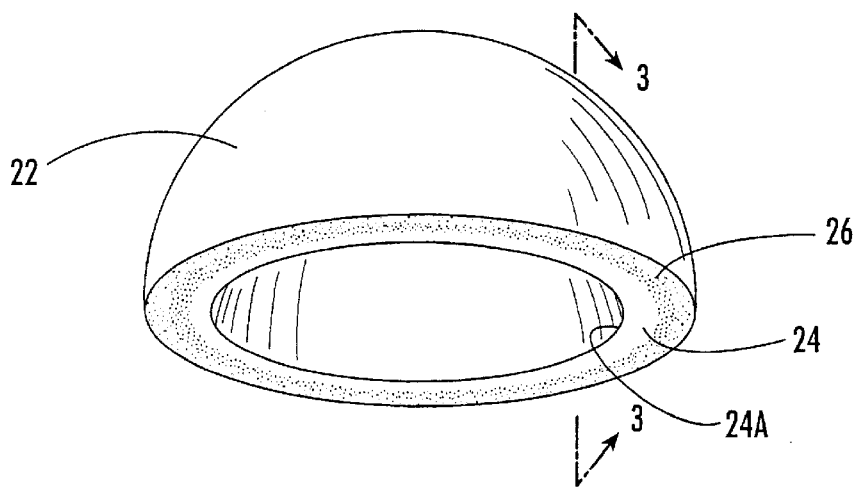
FIG. 2 is a perspective view of one embodiment of a precoated polymeric prosthesis made in accordance with the present invention.
Figure 3:
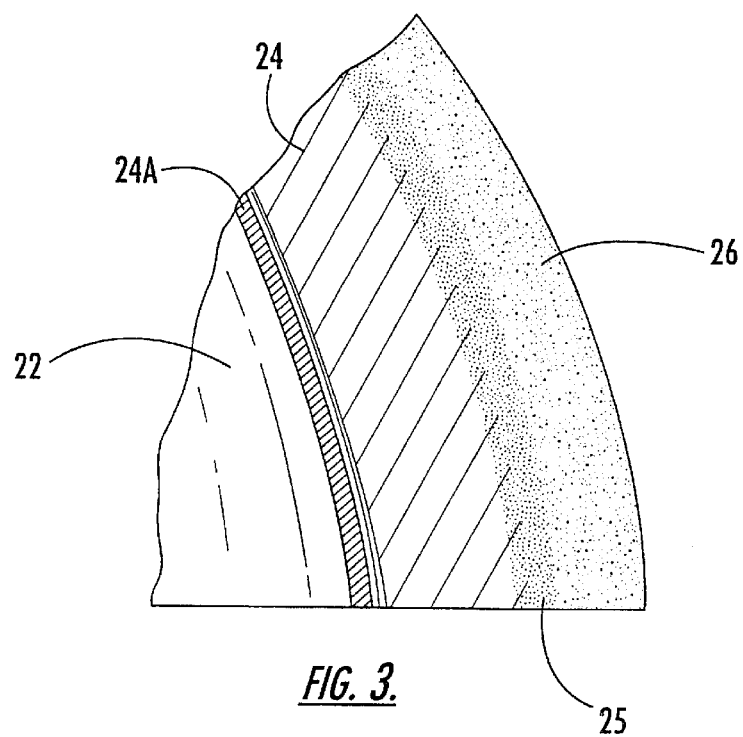
FIG. 3 is a partial cross-sectional view taken along line 3—3 of FIG. 2.

Acetabular cup 22 is made from an underlying polymeric portion 24 bonded to a bone cement compatible polymer coating 26 as more clearly shown in FIGS. 2 and 3. Coating 26 is cohesively bonded to polymeric portion 24. As shown in FIG. 1, bone cement compatible coating 26 is in turn bonded to a bone cement 28 which affixes acetabular cup 22 to a hip bone 30.

As described above, bone cement compatible polymer coating 26 can be applied to polymeric portion 24 to form a stiffness gradient for buffering stress transfer from acetabular cup 22 to bone cement 28. As shown in FIG. 3, acetabular cup 22 defines an interfacial region 25 extending between polymeric portion 24 and bone cement compatible polymer coating 26. Interfacial layer 25 represents the area in which coating 26 is cohesively bonded to polymeric portion 24. More particularly, across interfacial layer 25, there is a gradual increase in the concentration of the bone cement compatible polymer and there is a gradual decrease in the concentration of the polymer used to construct polymeric portion 24. This concentration gradient translates into a stiffness gradient as described above.

Figure 4:
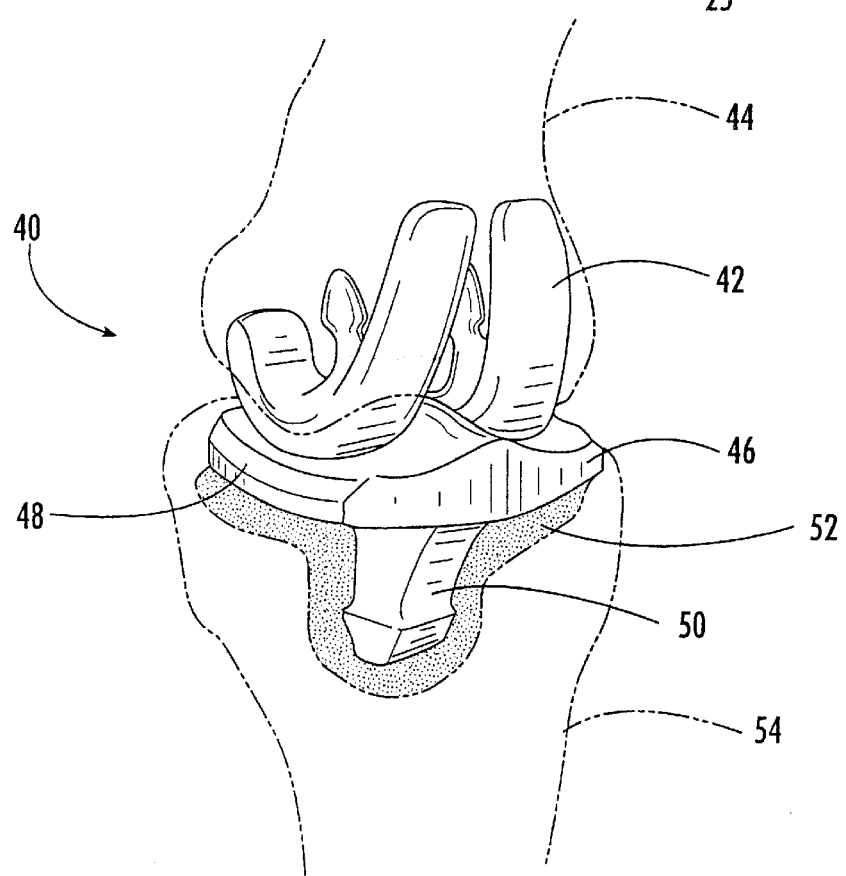
FIG. 4 is a perspective view of a knee implant, illustrating another embodiment of the present invention.

Besides an acetabular cup, a polymeric implant made according to the present invention is also particularly well suited for use as a tibia plateau in a knee replacement as illustrated in FIG. 4. As shown, knee replacement generally 40 includes a condylar implant 42 attached to a femur bone 44. In most applications, condylar implant 42 is made from a metal and is secured to femur 44 by screws or through the use of a bone cement.

Adjoining condylar implant 42 in FIG. 4 is a tibia plateau 46 made in accordance with the present invention. Tibia plateau 46 includes a top portion 48 and a stem portion 50. In one preferred embodiment, tibia plateau 46 is made from ultra high molecular weight polyethylene. At least stem portion 50 and the bottom of top portion 48 of tibia plateau 46 define a sintered precoat layer comprising in part a bone cement compatible polymer, such as polymethyl methacrylate in combination with a structural polymer such as UHMWPE. The precoating is subsequently bonded to bone cement 52 when implanted into a tibia 54. The precoating provides higher interfacial strength between the polyethylene polymer and the bone cement, thereby preventing loosening of the implant over time.

Figure 5:
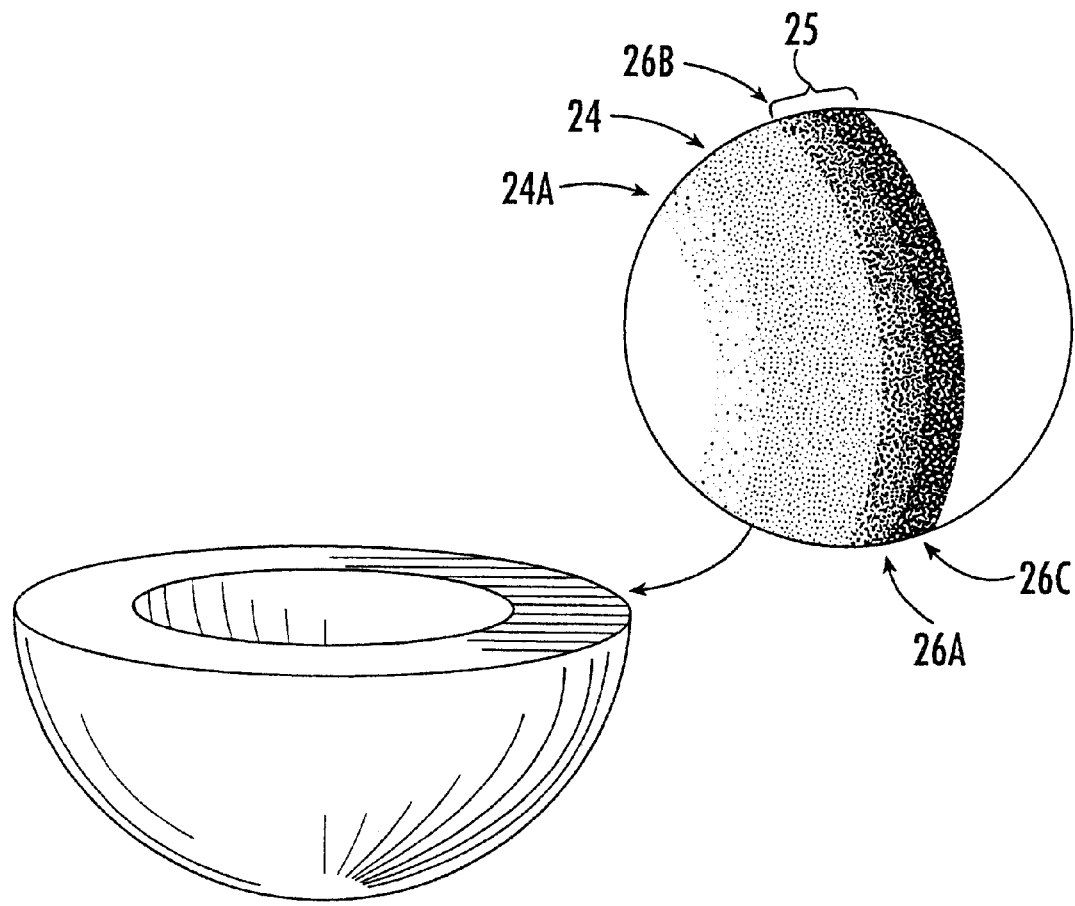
FIG. 5 is an enlargement of the indicated cross-sectional view the pre-coated surface layers of one embodiment of a polymeric prosthesis indicating details of a preferred sintered precoat composition.

As best seen in FIG. 5, a preferred embodiment of a bone cement compatible coating is set forth in reference to an acetabular cup 22. The polymeric cup 24 is typically provided by virgin polyethylene and has a thickness of between 3–15 mm. An innermost layer 24A of cross-linked polyethylene may be added to improve the wear properties. Layer 24A is added by addition of a PE powder layer which is chemically cross-linked to the polymer 24. Cross-linking may be carried out by use of a silane cross-linking agent, the use of U.V. radiation, sulfur vulcanization or other conventional cross-linking methods.

The outer polymeric cup surface is bonded to a bone cement compatible coating 26. Preferably, the coating layer 26 defines a interfacial gradient which comprises an innermost layer 26A of the activated powder. An adjacent, outer layer 26B of UHMWPE fibers may be provided. Fiber layer 26B has a thickness of between about 1–2 mm and reinforces useful cup mechanical properties and prevents creep of the prosthesis following implantation.

A final, outermost layer 26C of coating composition comprises a layer of PMMA. The outermost coating may comprise a layer of pure PMMA if applied as a separate layer and step. The outermost layer may also comprise a melted mixture of the sintered activated powder, UHMWPE fibers virgin polyethylene, cross-linked polyethylene, PMMA, and combination thereof. The outermost coating layer(s) are compatible with the PMMA-based bone cements and provides a stronger bond than can be achieved by direct bonding to a polymeric prosthesis.

While the interfacial layer helps improve the mechanical properties of the prosthesis, the preferred materials which form the interfacial layer do not ordinarily bond well to a PMMA-based bone cement. Accordingly, a preferred embodiment of the present invention provides a sintered layer 26 of a PMMA/UHMWPE activated powder. As illustrated, an outermost layer 26A of PMMA is added and sintered along with the activated powder of layer 26. The finished molded product thereby has a outer coating of PMMA sintered to the surface of the prosthesis along with a transition layer of an activated mixture of UHMWPE and PMMA powders. The transition layer of the sintered activated powder mixture is compatible with additional materials, such as polyethylene fibers, which may be incorporated into the final coating composition as part of an interfacial layer.

The present invention may be better understood with reference to the following examples. The examples make use of the same materials used in the prosthetic implant process, but are better suited for comparative analysis.

EXAMPLE NO. 1

Figure 6:
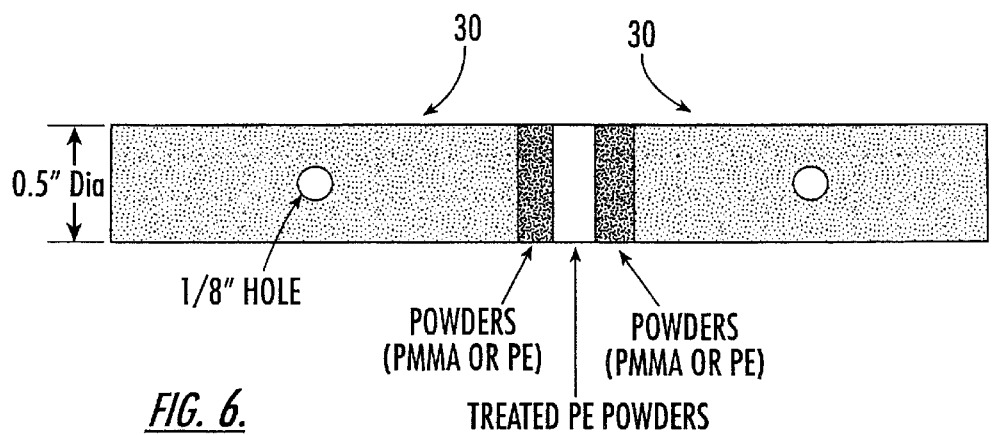
FIG. 6 is a schematic diagram of rods of polymeric materials as treated, bonded, and evaluated in accordance with the present invention.

A molded article was prepared in order to calculate and evaluate the tensile strength of molded materials using the activated powder to provide a precoat. The above materials and protocols were evaluated using rods of UHMWPE or PMMA. As seen in reference to FIG. 6, two cylindrical rods 30 are joined end to end using activated powder coatings compositions along with additional layers of pure UHMWPE powder and/or PMMA powder. The rod material and coating layer compositions used to make the sintered interconnections between the rods are set forth in Table 1.

The rods and coatings were sintered under the temperatures and pressures set forth in Table 1. The mold was held within an environmental control chamber and subjected to a dry nitrogen atmosphere during the compression molding steps. Control rods constructed of UHMWPE and PMMA were used to determine the interfacial strength of the rod material. For example, as seen in samples 4–6 on Table 1, UHMWPE rods were used to evaluate sinter strength of an activated mixture of UHMWPE and PMMA powder. Two UHMWPE rods of 0.5" diameter were coated with a first layer of unmodified UHMWPE powder, followed by a intervening layer of activated powder prepared as described above. The resulting sandwich construction of PE rod/PE powder/activated PE & PMMA powder/PE powder/PE rod (FIG. 6) was sintered in a dry nitrogen atmosphere in a heated mold at a constant pressure of 38.8 MPA for 60 minutes at the respective temperatures set forth in Table 1.

A control rod constructed of unmodified UHMWPE powder sintered between two rods of UHMWPE was used for data comparison. The interfacial strength (MPA) for the samples was determined by a Materials Testing Machine (MTS Model 810) which measured the tensile strength of the sintered bond between the activated UHMWPE and the untreated powder. Specifically, a constant cross-head speed of 0.1 mm/sec was applied to each sample until failure occurred. The test results are listed in Table 1.

The results indicate that the interfacial tensile strength increases with temperatures up to 166.5 degrees C. It was determined that the melting temperature of the coated powder composition as determined by a scanning calorimeter was 140 degrees C. The lower sintering pressure values provided strong interfacial tensile strength values. The data obtained from higher pressure values (sample 6) suggests that excess pressure results in a weaker bond, perhaps due to a restriction of the movement or rotation of polymer chains. The restriction would cause less diffusion through the interface. The depth of diffusion correlates with the strength of the resulting interface.

The high interfacial strength values obtained (16.3 Mpa) by the present compositions are significantly higher than report interfacial tensile strength values reported for a typical prosthesis-cement interface.

One important aspect of the present invention is the ability to provide the activated mixture of the PMMA-MMA treated UHMWPE powder. Scanning electron microscopy of untreated UHMWPE powder reveals an aggregate of nodules interconnected by fine fibrils and having an overall porous structure with a high surface area. Following treatment, the activated powder analysis shows that PMMA has penetrated deep within the porous structure of UHMWPE.

On sintered samples, surface features of the SEM samples indicate that interfacial bonding, as noted by jagged, torn surfaces, occurred between the PMMA and UHMWPE powders. The fine fibrils associated with pure UHMWPE powder is largely absent from the sintered composition. There is clear evidence that the PMMA diffusion from the treated powder to the UHMWPE powder layer.

From the data and observations made, it appears that several types of bonds occur within the interface of the coating composition. Chemical bonding between the UHMWPE and PMMA is believed to occur. Further, mechanical bonding is present as the result of the high pressure and temperature sintering conditions. It is believed that the combination of the chemical bonds and mechanical bonds contribute to the interfacial strength of the sintered materials.

While not separately quantified and reported herein, it has been observed that a PMMA-based bone cement provides a strong bond with a PMMA coating present on the exterior of a prosthesis. For instance, applicant's prior published studies in this area establishes the strong bond which occurs between an PMMA coating on a metal prosthesis and the PMMA bone cement. (Park, J. B., Malstrom, C. S. and von Recum, A. F., *Intramedullary Fixation of Implants Pre-Coated with Bone Cement: A Preliminary Study*, Biomaterials Medical Devices and Artificial Organs, 6, 361–373, 1978.) Accordingly, a similar strong bond has been exhibited between the outermost PMMA layer of the sintered coating and the PMMA bone cement. The present invention provides a process and composition which facilitates a stronger bond between a polymeric prosthesis and the bone cement. The composition provides both a chemical and structural transition zone which improves the physical wear properties of the resulting prosthetic implant and increases the bond strength between the implant and the bone cement.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

member being adapted to be attached to an adjoining bone with a bone cement;

applying a coating of a bone cement compatible polymer comprising an activated mixture of UHMWPE and PMMA to at least a portion of said polymeric member of said prosthesis; and sintering said coating of said bone cement compatible polymer to said portion of said polymeric member.

2. A process as defined in claim 1, wherein said polymeric member comprises ultrahigh molecular weight polyethylene.

3. A process as defined in claim 1, wherein said coating of said bone cement compatible polymer comprises a plurality of sintered coatings, said plurality of coatings is up to about 2 millimeters thick.

4. A process as defined in claim 1, wherein said coating of said bone cement compatible polymer has a substantially pore free outer surface.

5. A process as defined in claim 1, wherein said prosthesis is made entirely of a polymer.

6. A process as defined in claim 1, wherein said coating of said bone cement compatible polymer is sintered upon said polymeric member of said prosthesis according to the following steps:

contacting said polymeric member with an activated mixture of PMMA and UHMWPE powder, thereby forming a surface layer of activated powder;

sintering said surface layer to said polymeric member, thereby providing a melted surface coating of UHMWPE and PMMA, said coating compatible with a bone cement.

7. A process as defined in claim 6, wherein said activated mixture is provided by a process of comprising:

combining UHMWPE powder with an excess of MMA liquid monomer;

removing said MMA monomer from said UHMEPE powder;

mixing said UHMWPE powder with an excess of a liquid MMA+PMMA stock solution;

drying said UHMWPE powder, thereby providing an activated powder of UHMWPE and PMMA.

8. A process for coating a polymeric prosthesis with a bone cement compatible polymer prior to implantation for

TABLE 1

| Sample No. | Sintered Layers | Sintering Pressure (MPa) | Sintering Temp (° C.) | PE Powder Treatment | Interfacial Tensile Strength (MPa) |
|---|---|---|---|---|---|
| 1 | PE rod/PE powder/Treated PE powder/PE powder/PE rod | 38.7 | 134.1 | MMA + MMA/PMMA + BPO | 11.5 ± 0.71 |
| 2 | Same as above | 38.7 | 150.6 | Same as above | 15.1 ± 0.74 |
| 3 | Same as above | 38.7 | 166.5 | Same as above | 16.3 ± 0.94 |
| 4 | Same as above | 38.7 | 182.0 | Same as above | 16.3 ± 0.33 |
| 5 | Same as above | 19.7 | 166.5 | Same as above | 16.2 ± 0.92 |
| 6 | Same as above | 77.4 | 166.5 | Same as above | 14.2 ± 1.08 |
| 7 | PE rod/PE powder/PE rod | 38.7 | 166.5 | — | 19.9 ± 0.70 |
| 8 | PE rod (not sintered) | — | — | — | 21.5 ± 1.07* |

*Tensile yield strength

What is claimed is:

1. A process for coating a polymeric prosthesis prior to being implanted into the body, said process comprising the steps of:

providing a prosthesis having a shape configured to be implanted into a prepared area of the body, said prosthesis including a polymeric member, said polymeric improving the bond between said prosthesis and a bone cement, said process comprising the steps of:

providing a prosthesis made from a polymer;

contacting a portion of a surface of said prosthesis with an activated powder mixture of UHMWPE and PMMA; and, bonding said activated mixture to said portion of a surface of a prosthesis through a combination of heat and pressure, thereby providing a coating compatible with a bone cement.

9. A process as defined in claim 8, wherein said prosthesis is made from a polymer comprising polyethylene.

10. A process as defined in claim 9, wherein said activated powder is provided by a process comprising:
   combining UHMWPE powder with an excess of MMA liquid monomer;
   removing said MMA monomer from said UHMWPE powder;
   mixing said UHMWPE powder with an excess of a liquid MMA+PMMA stock solution;
   drying said UHMWPE powder, thereby providing an activated powder mixture of UHMWPE coated with PMMA.

11. A process as defined in claim 10, wherein said liquid MMA+PMMA stock solution is about a 9:1 volume to weight ratio of MMA to PMMA.

12. A process as defined in claim 8, wherein said bonding step further comprises sintering at a temperature greater than 150 degrees C.

13. A process as defined in claim 8, wherein said bonding step further comprises supplying a pressure of about at least 20 MPa.

14. A process as defined in claim 8, further comprising the step of providing an interfacial layer between said surface of said prosthesis and said coating, said interfacial layer selected from the group of virgin polyethylene, cross-linked polyethylene, polyethylene fibers, and combinations thereof.

15. A process as defined in claim 14, further comprising the step of providing an interfacial layer comprising cross-linking polyethylene to the surface layer of a polyethylene prosthesis.

* * * * *